US00PP15320P2

(12) United States Plant Patent
Oliver

(10) Patent No.: US PP15,320 P2
(45) Date of Patent: Nov. 16, 2004

(54) ***HEUCHERA* PLANT NAMED 'HEARTS ON FIRE'**

(50) Latin Name: *Heuchera×hybrida*
Varietal Denomination: Hearts on Fire

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 10/775,947

(22) Filed: Feb. 10, 2004

(51) Int. Cl.[7] ..... A01H 5/00

(52) U.S. Cl. ..... Plt./263
(58) Field of Search ..... Plt./263

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Heuchera* plant named 'Hearts on Fire', characterized by its full, densely foliated and uniformly mounded plant habit; upper surfaces of leaves silvery in color; lower leaf surfaces red purple in color; numerous showy white-colored flowers arranged on mostly erect panicles; red purple-colored flower buds, peduncles and pedicels; and excellent garden performance.

2 Drawing Sheets

Botanical classification/cultivar designation: *Heuchera× hybrida* cultivar Hearts on Fire.

BACKGROUND OF THE INVENTION

The present invention relates to a new and distinct cultivar of *Heuchera* plant, botanically known as *Heuchera×hybrida* and hereinafter referred to by the name 'Hearts on Fire'.

The new *Heuchera* is a product of a planned breeding program conducted by the Inventor in Scottdale, Pa. The objective of the breeding program is to create new *Heuchera* cultivars having good plant vigor, dense and uniform plant habit; and showy and attractive flower and leaf coloration.

The new *Heuchera* was discovered by the Inventor in a controlled environment in Scottdale, Pa., from seedling progeny from a cross-pollination made by the Inventor in May, 1999, of the *Heuchera×hybrida* cultivar Silver Maps, not patented, as the female, or seed, parent with a proprietary *Heuchera×hybrida* selection identified as code number H98-13A, not patented, as the male, or pollen, parent. The new *Heuchera* was selected by the Inventor in May, 2000. The selection of this plant was based on its desirable flower and foliage coloration.

Asexual reproduction of the new *Heuchera* by cuttings in a controlled environment in Scottdale, Pa., since September, 2000, has shown that the unique features of this new *Heuchera* are stable and reproduced true to type in successive generations.

SUMMARY OF THE INVENTION

The cultivar Hearts on Fire has not been observed under all possible environmental conditions. The phenotype may vary somewhat with variations in environment such as temperature and light intensity, without, however, any variance in genotype.

The following traits have been repeatedly observed and are determined to be the unique characteristics of 'Hearts on Fire'. These characteristics in combination distinguish 'Hearts on Fire' as a new and distinct cultivar of *Heuchera:*

1. Full, densely foliated and uniformly mounded plant habit.

2. Upper surfaces of leaves silvery in color; lower leaf surfaces red purple in color.
3. Numerous showy white-colored flowers arranged on mostly erect panicles.
4. Red purple-colored flower buds, peduncles and pedicels.
5. Excellent garden performance.

Plants of the new *Heuchera* can be compared to plants of the female parent, the cultivar Silver Maps. In side-by-side comparisons conducted by the Inventor in Scottdale, Pa., plants of the new *Heuchera* differed from plants of the cultivar Silver Maps in the following characteristics:

1. Plants of the new *Heuchera* were more densely foliaged than plants of the cultivar Silver Maps.
2. Leaves of plants of the new *Heuchera* had ruffled margins whereas leaves of plants of the cultivar Silver Maps did not have ruffled margins.
3. Flowers of plants of the new *Heuchera* had larger petals, shorter calyxes and longer pedicels than flowers of plants of the cultivar Silver Maps.

Plants of the new *Heuchera* can be compared to plants of the male parent selection. In side-by-side comparisons conducted by the Inventor in Scottdale, Pa., plants of the new *Heuchera* differed from plants of the male parent selection in the following characteristics:

1. Plants of the new *Heuchera* were shorter and more densely foliated than plants of the male parent selection.
2. Plants of the new *Heuchera* and the male parent selection differed in foliage, flower bud, peduncle and pedicel coloration.
3. Plants of the new *Heuchera* had longer inflorescences than plants of the male parent selection.

Plants of the new *Heuchera* can be compared to plants of the cultivar Silver Scrolls, disclosed in U.S. Plant Pat. No. 12,066. In side-by-side comparisons conducted by the Inventor in Scottdale, Pa., plants of the new *Heuchera* differed from plants of the cultivar Silver Scrolls in the following characteristics:

1. Plants of the new *Heuchera* were smaller and more densely foliated than plants of the cultivar Silver Scrolls.

2. Leaves of plants of the new *Heuchera* were smaller than leaves of plants of the cultivar Silver Scrolls.
3. Leaves of plants of the new *Heuchera* had ruffled margins whereas leaves of plants of the cultivar Silver Scrolls did not have ruffled margins.
4. Inflorescences of plants of the new *Heuchera* were shorter and more open than inflorescences of plants of the cultivar Silver Scrolls.

Plants of the new *Heuchera* can also be compared to plants of the cultivar Jade Gloss, disclosed in U.S. Plant Pat. No. 13,137. In side-by-side comparisons conducted by the Inventor in Scottdale, Pa., plants of the new *Heuchera* differed from plants of the cultivar Jade Gloss in the following characteristics:

1. Plants of the new *Heuchera* were smaller and more densely foliated than plants of the cultivar Jade Gloss.
2. Leaves of plants of the new *Heuchera* were smaller than leaves of plants of the cultivar Jade Gloss.
3. Leaves of plants of the new *Heuchera* had ruffled margins whereas leaves of plants of the cultivar Jade Gloss did not have ruffled margins.
4. Flowers of plants of the new *Heuchera* had larger petals than flowers of plants of the cultivar Jade Gloss.

BRIEF DESCRIPTION OF THE PHOTOGRAPHS

The accompanying colored photographs illustrate the overall appearance of the new *Heuchera*, showing the colors as true as it is reasonably possible to obtain in colored reproductions of this type. Colors in the photographs may differ slightly from the color values cited in the detailed botanical description which accurately describe the colors of the new *Heuchera*.

The photograph on the first sheet comprises a side perspective view of a typical one-year old flowering plant of 'Hearts on Fire'.

The photograph on the second sheet is a close-up view of a typical inflorescence of 'Hearts on Fire'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following detailed botanical description describe plants grown in Scottdale, Pa. during the summer in a glass-covered greenhouse and under cultural conditions which approximate commercial practice. Plants were grown as single plants in one-gallon containers and were about one year old. During the production of the plants, day temperatures ranged from 15 to 26° C. and night temperatures ranged from 5 to 15° C.

Botanical classification: *Heuchera×hybrida* cultivar Hearts on Fire.

Parentage:

*Female, or seed, parent.*—*Heuchera×hybrida* cultivar Silver Maps, not patented.

*Male, or pollen, parent.*—Proprietary *Heuchera×hybrida* selection identified as code number H98-13A, not patented.

Propagation:

*Type.*—By cuttings.

*Time to initiate roots.*—Summer: About 15 days at 23° C. Winter: About 21 days at 17° C.

*Time to produce a rooted cutting.*—Summer: About 45 days at 23° C. Winter: About 60 days at 17° C.

*Root description.*—Fine, fibrous and white in color.

*Rooting habit.*—Freely branching.

Plant description:

*Appearance.*—Perennial; basal rosette plant habit with leaves developing from the base; densely foliated; full, mounded and uniform plant habit with mostly upright panicles with white-colored flowers. Vigorous growth habit.

*Plant size.*—Height, soil level to top of foliar plane: About 10 cm. Height, soil level to top of panicles: About 50 cm. Diameter or spread: About 30 cm.

*Foliage description.*—Arrangement: Basal rosette, simple. Length: About 6 cm. Width: About 5 cm. Shape: Rounded cordate; seven-lobed. Apex: Obtuse. Base: Auriculate. Margin: Crenate with fine ciliation; ruffled. Texture, upper surface: Slightly rough; glabrous. Texture, lower surface: Slightly pubescent. Venation pattern: Palmate, reticulate. Color: Developing leaves, upper surface: 198A underlain with 187B. Developing leaves, lower surface: 187B. Fully expanded leaves, upper surface: 198A. Fully expanded leaves, lower surface: 187B. Venation, upper surface: 189A underlain with 200A. Venation, lower surface: 187B. Petiole: Length: About 8 cm. Diameter: About 1.2 mm. Texture, upper and lower surfaces: Pubescent. Color, upper and lower surfaces: 198A underlain with 187B.

Flower description:

*Appearance/arrangement.*—Single campanulate flowers arranged on numerous mostly erect panicles; about 83 flowers and flower buds per flowering stem. Flowers face outward to slightly upright. Flowering continuous. Flowers persistent. Flowers not fragrant.

*Time of flowering.*—Plants flower June and July in Scottdale, Pa.

*Inflorescence longevity.*—Individual inflorescences last about one week on the plant.

*Inflorescence size.*—Length: About 50 cm. Diameter: About 8 cm.

*Flower size.*—Diameter: About 4 mm. Depth (height): About 7 mm.

*Flower buds.*—Height: About 5 mm. Diameter: About 3.5 mm. Shape: Globular. Color, at stage of showing color: 59B.

*Sepals.*—Quantity/arrangement: Five sepals; radially symmetrical and fused at base. Calyx length: About 5.5 mm. Calyx diameter: About 4 mm. Shape: Elongate. Apex: Obtuse. Margin: Entire. Texture, upper and lower surfaces: Pubescent. Color, upper surface: Close to 155D. Color, lower surface: 57B.

*Petals.*—Quantity/arrangement: Five minute petals; radially symmetrical. Length: About 4 mm. Width: About 1.5 mm. Shape: Spatulate. Apex: Acute. Margin: Entire. Texture, upper and lower surfaces: Smooth, glabrous. Color, upper and lower surfaces: Close to 155D.

*Flower bracts.*—Length: About 4.6 mm. Width: About 1 mm. Shape: Subulate. Apex: Acute. Margin: Serrate. Texture, upper and lower surfaces: Pubescent. Color, upper and lower surfaces: 57A.

*Peduncle.*—Strength: Strong. Aspect: Upright to angled outwardly to 30° from vertical. Length: About 25 cm. Diameter: About 1.1 mm. Texture: Smooth. Color: 57A.

*Pedicels.*—Strength: Strong. Aspect: Erect to about 30° from vertical. Length: About 3 mm. Diameter: About 0.2 mm. Texture: Pubescent. Color: 198C underlain with 57B.

*Reproductive organs.*—Androecium: Stamen number: Five per flower. Anther shape: Oval. Anther length: About 0.2 mm. Anther color: 23B. Amount of pollen: Scarce. Pollen color: 23A. Gynoecium: Pistil number: Two per flower. Pistil length: About 5 mm. Stigma shape: Round. Stigma color: 157C. Style length: About 3.5 mm. Style color: 157C. Ovary color: 158C.

*Seed.*—Size: About 0.3 mm by 0.6 mm. Color: Close to 202A.

Disease/pest resistance: Resistance to pathogens and pests common to *Heuchera* has not been observed on plants grown under commercial conditions.

Weather/temperature tolerance: Plants of the new *Heuchera* have been observed to have excellent garden performance. Plants of the new *Heuchera* have demonstrated good tolerance to rain, wind, night temperatures as low as −35° C., and day temperatures as high as 45° C.

It is claimed:

1. A new and distinct cultivar of *Heuchera* plant named 'Hearts on Fire', as illustrated and described.

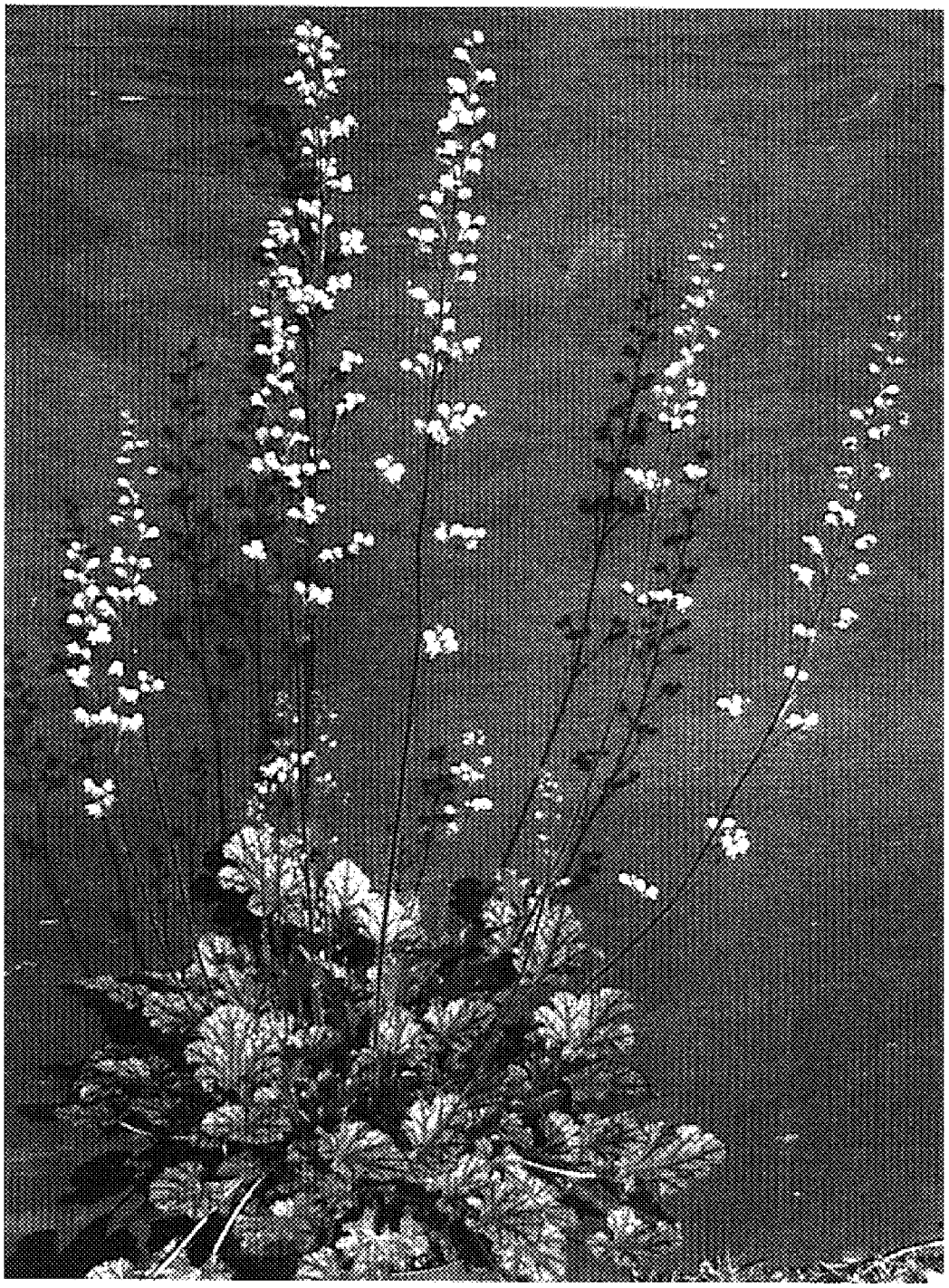

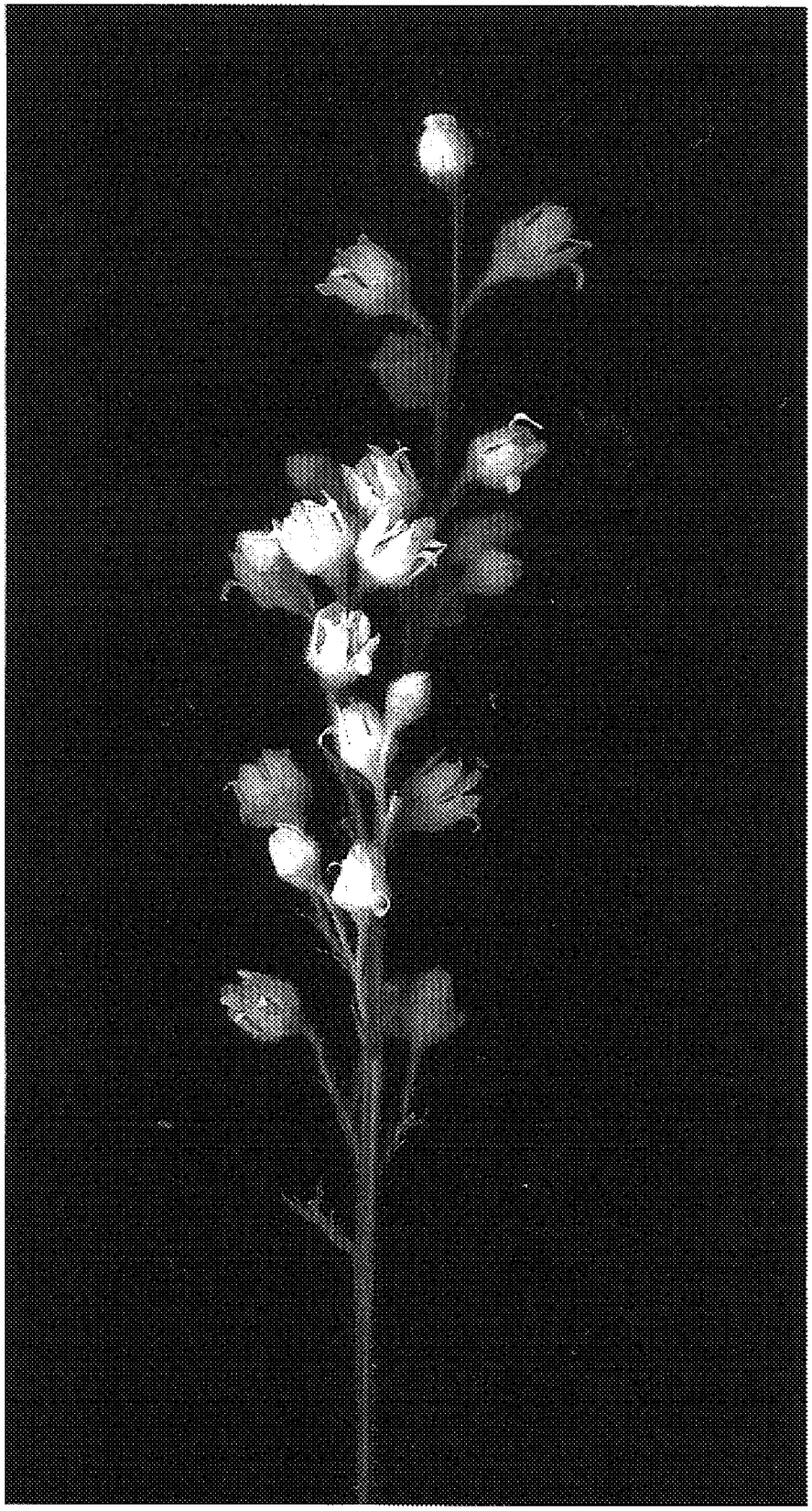

* * * * *